United States Patent [19]

Geweke

[11] Patent Number: 5,187,435
[45] Date of Patent: Feb. 16, 1993

[54] NON-DESTRUCTIVE TEST APPARATUS WITH EDDY CURRENT TRANSDUCER ROTARY HEAD AND FIELD HOMOGENIZING CONDUCTIVE RING FOR SCANNING METAL TEST MATERIALS

[75] Inventor: Werner Geweke, Reutlingen, Fed. Rep. of Germany

[73] Assignee: Dr. Friedrich Forster Pruferatebau GmbH & Co. KG, Reutlingen, Fed. Rep. of Germany

[21] Appl. No.: 721,468

[22] PCT Filed: Oct. 10, 1990

[86] PCT No.: PCT/EP90/01696
§ 371 Date: Jul. 5, 1991
§ 102(e) Date: Jul. 5, 1991

[87] PCT Pub. No.: WO91/07656
PCT Pub. Date: May 30, 1991

[51] Int. Cl.⁵ .............................................. G01N 27/90
[52] U.S. Cl. .................................. 324/225; 324/232; 324/242; 324/262
[58] Field of Search ........ 324/225, 226, 227, 232-238, 324/240, 242, 243, 262

[56] References Cited

U.S. PATENT DOCUMENTS

| 3,299,349 | 1/1967 | Tompkins et al. ................... 324/262 |
| 4,596,953 | 6/1986 | Nagasaka et al. ............... 324/262 X |
| 4,673,879 | 6/1987 | Harris et al. ...................... 324/262 X |
| 5,023,550 | 6/1991 | Yamazaki et al. ................... 324/262 |

FOREIGN PATENT DOCUMENTS 2905399 8/1979 Fed. Rep. of Germany.
3228382 2/1983 Fed. Rep. of Germany.

Primary Examiner—Gerard R. Strecker
Attorney, Agent, or Firm—George J. Netter

[57] ABSTRACT

A rotary head for scanning the surface of elongated test materials (62) by eddy current transducers (60) is additionally provided with means for magnetization of the test material (62) over an intended test range making it now possible to achieve sensitive testing of non-bare ferromagnetic bars and wires, testing for "smeared cracks" where surface has closed above the material separation, and testing of welded austenitic pipes. For the magnetization, parts of the housing (10) as well as a rotating hollow shaft (40) are employed in the conduction of magnetic flux, and special measures are taken for the homogenization of the magnetic field in the test range.

9 Claims, 3 Drawing Sheets

NON-DESTRUCTIVE TEST APPARATUS WITH EDDY CURRENT TRANSDUCER ROTARY HEAD AND FIELD HOMOGENIZING CONDUCTIVE RING FOR SCANNING METAL TEST MATERIALS

BACKGROUND OF INVENTION

1. Field of the Invention

The invention relates to a rotary head for scanning the surface of elongated metal test materials and, more particularly to such a rotary head in a non-destructive eddy current defect test apparatus.

2. Description of Related Art

For many years, rotary heads have been known for use in non-destructive testing of materials, and are widely used. They serve there for testing, in particular, of bare curved surface materials of steel and non-ferrous substances to detect defects located at any point below the surface and extending up to the surface. During long periods of application, such rotary heads have gained a high technological performance providing excellent results. On bare surfaces, e.g., cracks having a depth of only 30 micrometers can be reliably detected, and this accomplished at rather high running speeds.

On the other hand, there are present limits, which would be desirable to overcome, since this would lead to further possible applications. For instance, sensitive testing of "non-bare" ferromagnetic steel is not possible with known eddy current rotary heads because of the high interference level encountered. Another example relates to cracks in ferromagnetic materials, wherein further processing, as rolling, drawing or peeling, will result in a surface being closed again. In this case, the low penetration depth of eddy currents required for the high frequencies required to achieve desired sensitivity accounts for the fact that such "smeared" cracks are impossible to detect in most cases. Difficulties have also been encountered in the testing of welded austenitic pipes, wherein ferrous impurities are found to generate a high interference level in the area of the weld seam, and, therefore, prevent an efficient testing of such pipes.

SUMMARY OF THE PRESENT INVENTION

According to the invention, the test material is magnetized resulting in a considerable reduction of the magnetic permeability of the test material, and, if possible, magnetized to reach the saturation range. There is a risk, however, in doing this that the ferrite cores of eddy current transducers will also become saturated, and as a result that the sensitivity of the latter will be undesirably affected. This is compensated for in the invention by locating a ring of magnetically conductive material between the magnetization coil and the eddy current transducer. This ring homogenizes the magnetic field in the test range, and, therefore, the radial component of the magnetic field above the test material surface, will stay small.

By reducing the magnetic permeability of the test material, a comprehensive suppression of all interference sources caused by magnetic inhomogeneities of the material surface, such as scale, heat zones, weld seams or cold consolidation, for example, is achieved. It is now possible, for the first time, to also test "non-bare" ferromagnetic material, using rotating eddy current probes. For "smeared cracks" (i.e. with closed surfaces) the strong reduction of the magnetic permeability, which may be 50 times or more, causes a corresponding increase in the penetration depth of the eddy currents, making defects detectable, which would have normally remained hidden. Also, now for the first time welded austenitic pipes are now fully accessible to testing with eddy current rotary heads, since by the reduction of the magnetic permeability, the influence of ferrous impurities can be made ineffective.

A first embodiment of the invention provides interchangeable protective sleeves supported by the housing and having a borehole adapted to the diameter of the test material, which sleeves serve as conductors of the magnetic flux. According to another embodiment, a protective sleeve extends into the borehole of a hollow shaft allowing the magnetic flux to be conducted in an optimum manner via the rotating hollow shaft into the test material. A still further embodiment requires that between the protective sleeve and the hollow shaft, there is provided a narrow air gap at least at one position, such that a low-loss transfer of the magnetic flux is possible.

According to a particularly advantageous and further embodiment of the invention, the homogenization ring covers the side of the magnetization coil directed toward the eddy current transducers up to a predetermined distance from the axis of rotation, which corresponds approximately to a maximum of double the radial distance of the eddy current transducers from the axis of rotation. An important aspect of this embodiment is that the homogenization ring is in magnetically conductive connection with those parts of the housing conducting the magnetic flux.

According to yet another aspect of the invention, the protective sleeves are totally or partially coated with a thin layer of magnetically non-conductive material thereby "sticking" of the magnetized ferromagnetic test material to the protective sleeves is prevented, and a smooth passage of the latter is achieved. A still further aspect of the invention comes about from the rotary section comprising a rotary disk rigidly connected to the hollow shaft, the rotary disk eddy current transducers being suspended, and the rotary disk being made of magnetically non-conductive material. Therefore, magnetic poles are prevented from being formed at the disk, and no eddy currents are produced in the adjacent housing sections, which would necessarily lead to heating-up and braking effects.

An essential aspect of the invention is that, in the test range covered by the apparatus magnetic field, there is also provided a stationary eddy current transducer assembly which may be integrally mounted onto the interior of a protective sleeve. In this way the space and cost-economical combination of stationary and rotating eddy current transducers is made possible in a simple manner. Therein, it is particularly advantageous that both can use the same d.c. pre-magnetization to lower the interference level.

A stationary eddy current transducer assembly can be adapted as either absolute-type as well as difference-type continuous coils. On the other hand, segment coils distributed over the transducer periphery can also be provided. Absolute-type coils can, in addition to the various defect test possibilities, now also detect material mistakes, e.g., thiciness. Difference-type continuous coils are particularly suitable for detecting external defects, holes in pipe walls and inclusions of foreign matter.

It is advantageous that the various systems can complement each other. Furthermore, for ferromagnetic material, stray flux coils can be used instead of the eddy current continuous coils. In the latter case, coils built up in a similar way as with the eddy current continuous coils, in that the same coils may also be used for simultaneous reception of eddy current and stray flux signals.

The d.c. pre-magnetization has, in addition to the objects already described, the additional object of producing a magnetic stray flux at the defect positions, which stray flux is detected by the coils mentioned above. Thus, the detection level for lateral cracks is further reduced. Beside external cracks, internal cracks are now also detectable and local wall thickness reductions can be detected as well.

DESCRIPTION OF THE PREFERRED EMBODIMENTS

Figure 1:
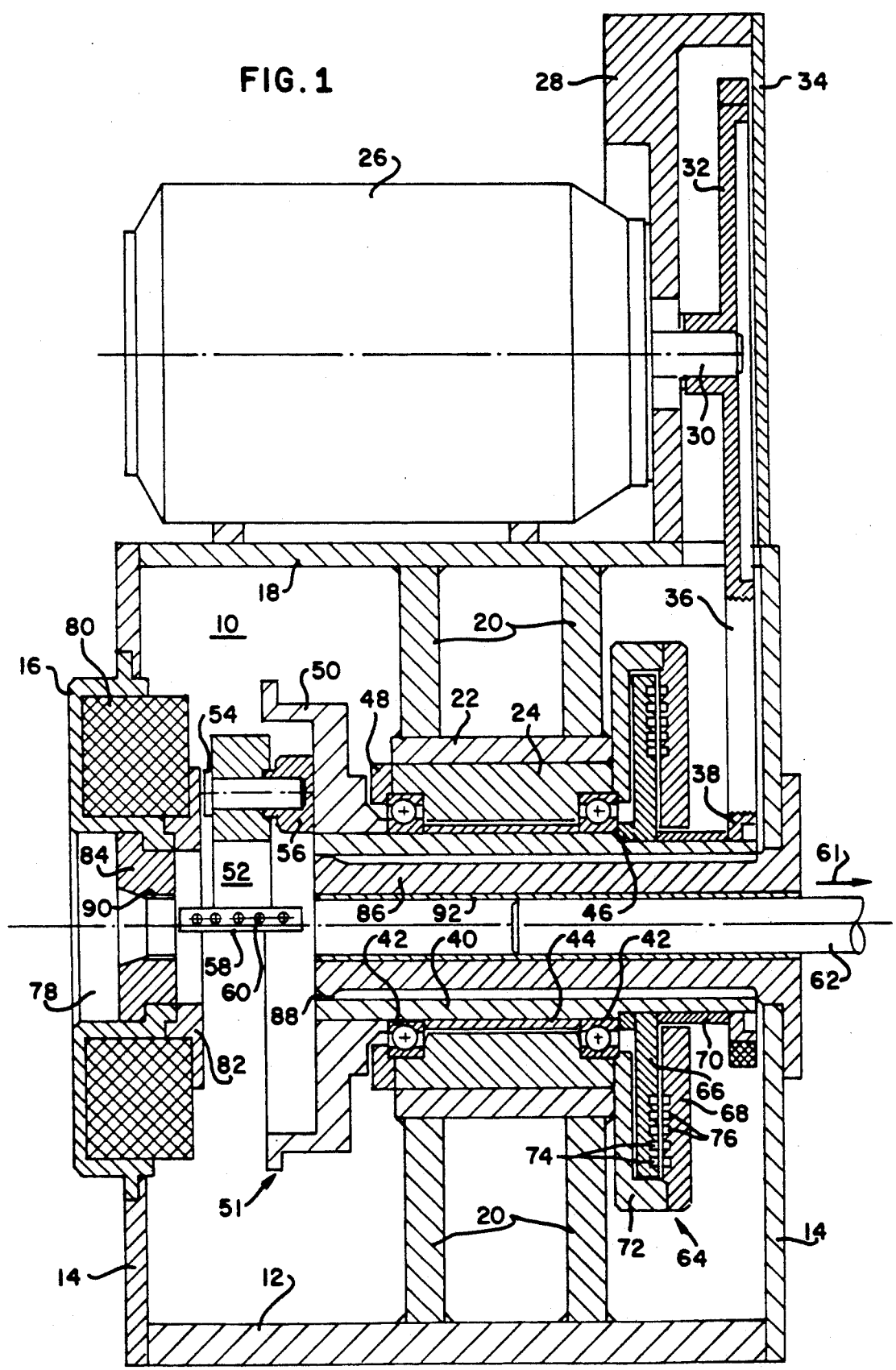
FIG. 1 depicts a rotary head in cross-section.
Figure 2:
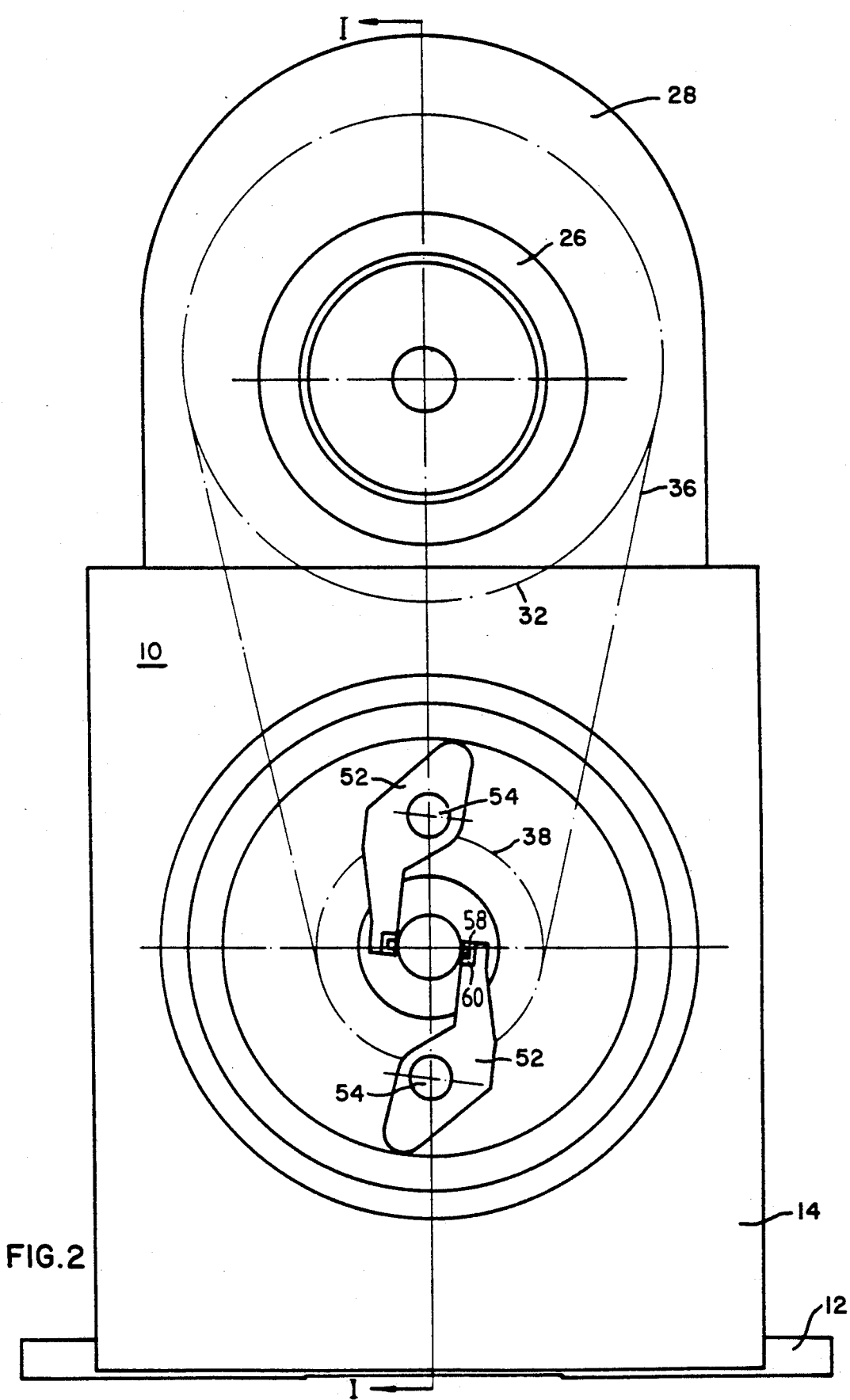
FIG. 2 shows the rotary head in a front elevational view.

Referring now to FIGS. 1 and 2, there is shown a rotary head in cross-section and in a front elevational view, respectively. A housing 10 including a base plate 12, walls 14, a housing plate 16, a cover plate 18, spars 20, a receiving body 22, and a bearing body 24 forms the bearing component of the rotary head. The mentioned parts of the housing 10 are made of ferromagnetic steel, and are connected to each other by welding or other suitable means. The cover plate carries a drive motor 26 secured to a flange plate 28. The rotational movement of the motor 26 is transferred from a drive shaft 30 to a drive wheel 32 which is protected against access by a cover 34. The drive belt 36 transfers the drive force to a driven wheel 38 unitarily connected to a hollow shaft 40. The hollow shaft 40 is supported in the bearing body 24 by two suitable roller bearings 42 which maintain each other over a ferromagnetic support bushing 44 and which are fixed to the hollow shaft 40 and to the bearing body 24 by rings 46 and 48, respectively. The air gap between the bearing body 24 and the support bushing 44 is small, in order that the magnetic flux will be subject to low impedance when passing from one to the other.

A rotary disk 50 of light metal is rigidly fixed to the hollow shaft 40. It forms, together with the hollow shaft 40 and the driven wheel 38, a rotary section 51. Two probe levers 52 are mounted in bearing blocks 56 to rotate about two pins 54, which bearing blocks are fixed to the rotary disk 50. For the sake of clarity, only one of the two probe levers 52 is shown in FIG. 1.

At the front end of the probe levers 52, a probe beam 58 is mounted carrying five eddy current transducers 60 which are located, during operation, immediately adjacent to the surface of the test material for scanning it in spiral tracks, when along with the rotating rotary section 51, the rotary head is passed by the test material. As an example of a test material, a generally cylindrical bar 62 leaving the rotary head in direction of arrow 61.

The signals of the rotating eddy current transducers 60 are conducted over a rotary transmitter assembly 64 to the outside, where they are connected by a cable to an electronic evaluator unit (both not shown). The rotary transmitter assembly may be of the type described in detail in a parallel patent application DE 36 32 395 comprising a rotor disk 66 and a stator disk 68, the former being rigidly connected to the hollow shaft 40 and secured by a bushing 70, and the latter being fixed by a carrying plate 72 to the receiving body and thereby located closely adjacent the rotary disk 66. The outputs of the eddy current transducers 60 are connected with primary windings 74 included in the rotor disk 66, whereas secondary windings 76 included in the stator disk 68 are conducted over a plug (not shown) connection to the cable mentioned above.

The housing plate 16 (omitted in FIG. 2 in order to show the probe levers 52) has to fulfill a double function. On one hand, it closes the opening in the front wall 14 except for a passage 78 through which the test material 62 passes. On the other hand, the plate space for receiving a magnetization coil 80 may be produced as a free-supporting winding introduced into the space of the housing plate 16 intended therefor, and held by a homogenization ring 82.

An additional feature of the homogenization ring 82 is explained as follows. Into the passage 78 of the housing plate 16 there is inserted a front protective sleeve 84. A rear protective sleeve 86 is fixed to the rear wall 14, and extends into the borehole of the hollow shaft 40. It is a primary object of both protective sleeves 84, 85 to guide the test material 62 safely. Furthermore, the protective sleeves 84, 86 are made from a magnetically conductive material to offer an important contribution for the conduction of the magnetic flux. The rear protective sleeve 86 comprises, for this latter purpose, at its front end a limited length portion having a slightly smaller diameter than that of the borehole of the hollow shaft 40, so that a narrow air gap 88 of low magnetic impedance is formed.

The protective sleeves 84, 86 are interchangeable, and provided with a precisely dimensioned selection of boreholes. Accordingly, on one hand, an accurate guiding of the test material 62 is achieved, and, on the other hand, an effective introduction of the magnetic flux into the test material is guaranteed. The magnetic flux generated in the magnetization coil 80 passes over the housing plate 16, front wall 14, base plate 12 and cover plate 18, respectively, or over the side walls, over the spars 20, receiving body 22, bearing body 24, support bushing 44 and hollow shaft 40. The immediate introduction of the magnetic flux into the test material 62 is performed, as mentioned above, via the protective sleeves 84, 86.

The boreholes of the protective sleeves 84, 86 are each coated with a thin layer of magnetically non-conductive material or, optionally as in the present example, abrasion-resistant sleeves 90 and 92, are provided. In this manner, it is achieved that the magnetized ferromagnetic test material will not "stick" in the interior of the protective sleeves 84, 86, and can be pulled through the rotary head without exhibiting a large resistance.

The test range, over which the test material 62 is fully magnetized, is limited, substantially, by the ends of the two protective sleeves 84, 86. The magnetic flux in the test range should be as homogeneous as possible, and, in particular, in the space above the test material 62 where the eddy current transducers 60 are located, the radial component of the magnetic field should be held within narrow limits. This is achieved by the introduction of the homogenization ring 82 absorbing a large fraction of the lines of force, which would otherwise, starting from the edge of the magnetization coil 80, be shunted immediately to the test material 62 or to the rear protective sleeve 86. In order that this measure will be effective even for the most unfavorable application, i.e. for the largest diameter of the test material, it is recommended to cover the magnetization coil 80 up to a distance from the axis of rotation by the homogenization ring, corresponding approximately to twice the maximum radial distance of the eddy current transducers 60 from the axis of rotation.

Figure 3:
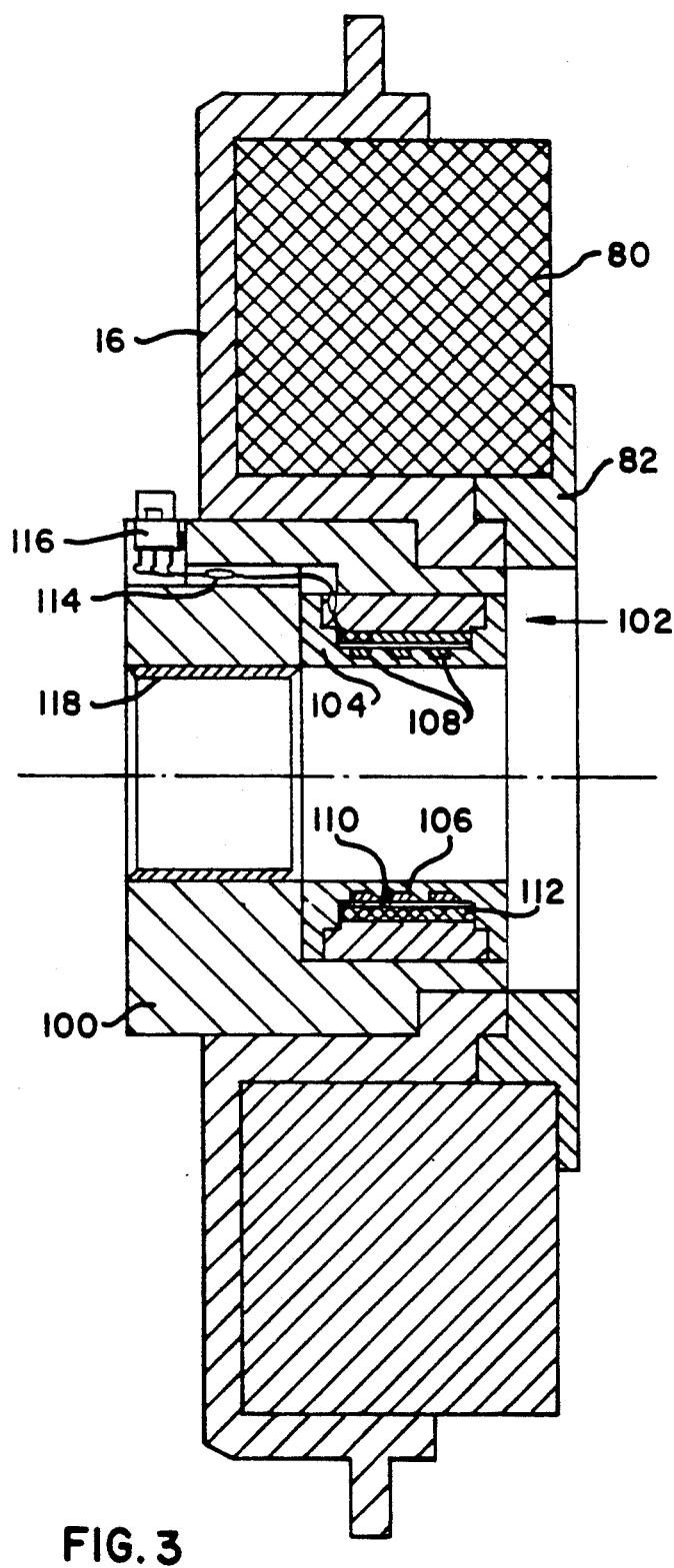
FIG. 3 is a detail of the rotary head in an alternative embodiment and to a different scale.

FIG. 3 refers to the case where, in addition to the rotating eddy current transducers 60, there are employed stationary eddy current transducers within sensing range of the object being tested. For this purpose, the front protective sleeve is of a different design. Since all other parts of the rotary head remain unchanged, only a modified protective sleeve 100 is shown mounted into the housing plate 16. The latter may, as was described above, be used in a rotary head according to FIGS. 1 and 2. The protective sleeve 100 is deeper on the right-hand side. The central free space accommodates the eddy current transducer assembly 102. The latter comprises a coil body 104 of a suitable insulating material. In the bottom of the coil body 104, there are provided three grooves, into each of which are inserted eddy current receiver coils 106, 108. One of these coils may be an absolute-type coil 106 whereas the two outer coils (108) may be differentially connected. An eddy current excitation coil 112 is wound on the receiver coils 106, 10B and separated therefrom by an insulating layer 110. Wires 114 connect the receiver coils 106, 108 and the excitation coil 112 with a junction box 116 allowing for the connection of the stationary eddy current transducer assembly 102 to an electronic unit. As described for the protective sleeves 84, 86, the protective sleeve 100, too, is protected by a thin sleeve 118 against magnetic "sticking".

Instead of the described eddy current transducer assembly 102 including the test material 62, there can also be mounted in the space provided within the protective sleeve 100, a set of eddy current segment coils distributed over the periphery. It is also possible to employ the described assembly of transducers 102 as stray flux transducers where magnetic flux generated in the test material 62 by the magnetization coil 80 produces magnetic stray fluxes at the defect positions. The stray fields can be detected, e.g., by the coil 106, and can be processed in known manner.

What is claimed is:
1. Apparatus for scanning the surface of elongated metal test material (62) by eddy current transducers (60), including a housing (10); a rotating rotary section (51) to which the eddy current transducers (60) are attached and which includes a hollow shaft (40) within the housing (10) for receiving the passage of the test material (62) therethrough; drive means (26) mounted on said housing (10) for producing rotational movement of the rotary section (51); and a rotary transmitter assembly (64) within the housing (10) and arranged about shaft (40) over which the eddy current transducers are electrically connected with an electronic evaluator unit, comprising:
  means for magnetizing the test material (62) in the longitudinal direction thereof within a given test range mounted to housing (10), including a hollow magnetization coil (80) within which the test material (62) is received for generating a magnetic flux;
  said eddy current transducers (60) arranged in sensing relation to the magnetized test material (62);
  conductors for connecting the magnetic flux into the test material (62), including portions of the housing (10) and the hollow shaft (40), each being made of magnetically conductive material; and
  magnetic field homogenization means including a homogenization ring (82) of magnetically conductive material surrounding the test material (62) and located between the magnetization coil (80) and the eddy current transducers (60) to compensate for saturation of the eddy current transducers.

2. Apparatus according to claim 1, in which interchangeable protective sleeves (84, 86, 100) within the housing (10) surround the test material as it passes through the housing and made of magnetically conductive material are provided as conductors for the magnetic flux, the boreholes thereof being adaptable to the diameters of the test material (62).

3. A rotary head according to claim 2, in which one of the protective sleeves (86) extends into the borehole of the hollow shaft (40).

4. A rotary head according to claim 3, in which a narrow gap (88) is provided between the protective sleeve (86) and the hollow shaft (40), at least at one position, for transferring the magnetic flux.

5. A rotary head according to claim 1, in which the homogenization ring (82) covers the side of the magnetization coil (80) directed toward the eddy current transducers (60) up to such a distance from the axis of rotation, corresponding approximately to twice the maximum radial distance of the eddy current transducer (60) from the axis of rotation.

6. A rotary head according to claim 1, in which the homogenization ring (82) is in magnetically conductive connection with the portions of the housing (10) conducting the magnetic flux.

7. A rotary head according to claim 1, in which the protective sleeves (84, 86, 100) are coated in their boreholes at least partially with a thin layer (90, 92, 118) of magnetically non-conductive material.

8. A rotary head according to claim 1, in which the rotary section (51) includes a rotary disk (50) rigidly connected to the hollow shaft (40) from which the eddy current transducers are suspended, which disk is made of magnetically non-conductive material.

9. Apparatus according to claim 1, in which a stationary eddy current transducer assembly (102) is mounted in the interior of a protective sleeve (100).

* * * * *